(12) United States Patent
Biesinger et al.

(10) Patent No.: US 11,874,218 B2
(45) Date of Patent: Jan. 16, 2024

(54) METAMATERIAL-BASED IR EMITTER HAVING MODULATABLE EMISSIVITY

(71) Applicant: Hahn-Schickard-Gesellschaft für angewandte Forschung e. V., Villingen-Schwenningen (DE)

(72) Inventors: Daniel Biesinger, Villingen-Schwenningen (DE); Achim Bittner, Heilbronn (DE)

(73) Assignee: Hahn-Schickard-Gesellschaft für angewandte Forschung e. V., Villingen-Schwenningen (DE)

(*) Notice: Subject to any disclaimer, the term of this patent is extended or adjusted under 35 U.S.C. 154(b) by 208 days.

(21) Appl. No.: 17/310,465

(22) PCT Filed: Feb. 11, 2020

(86) PCT No.: PCT/EP2020/053438
§ 371 (c)(1),
(2) Date: Aug. 4, 2021

(87) PCT Pub. No.: WO2020/165150
PCT Pub. Date: Aug. 20, 2020

(65) Prior Publication Data
US 2022/0107263 A1    Apr. 7, 2022

(30) Foreign Application Priority Data

Feb. 12, 2019 (EP) .................... 19156588

(51) Int. Cl.
*G01N 21/17* (2006.01)
*G01N 33/00* (2006.01)

(52) U.S. Cl.
CPC ..... *G01N 21/1702* (2013.01); *G01N 33/0027* (2013.01); *G01N 2021/1704* (2013.01); *G01N 2201/061* (2013.01)

(58) Field of Classification Search
CPC .......... G01N 21/1702; G01N 33/0027; G01N 2021/1704; G01N 2201/061;
(Continued)

(56) References Cited

U.S. PATENT DOCUMENTS

| | | | |
|---|---|---|---|
| 2006/0138327 A1* | 6/2006 | Kauppinen | G01N 21/1702 250/339.13 |
| 2017/0290098 A1* | 10/2017 | Kautzsch | H01L 33/642 |
| 2020/0018731 A1* | 1/2020 | Theuss | G01N 29/032 |

OTHER PUBLICATIONS

English Translation of International Search Report in PCT/EP2020/053438 dated Apr. 20, 2020.
(Continued)

*Primary Examiner* — Suman K Nath
(74) *Attorney, Agent, or Firm* — Knobbe Martens Olson & Bear LLP (57) ABSTRACT

The invention relates to a modulatable infrared emitter comprising a heating element, a planar base element, a dielectric interlayer, and a planar cover element which is a structured metamaterial, and an actuator, wherein the actuator is configured for a relative movement of the cover element and the base element between a first and a second position in order to modulate the intensity of the emission of the infrared emitter. The invention further relates to production methods for the infrared emitter, methods for the modulated emission of infrared red radiation by means of the infrared emitter, and preferred uses of the infrared emitter. A system comprising the infrared emitter and a control device for regulating the actuator are also preferably the subject matter of the invention.

20 Claims, 3 Drawing Sheets

(58) Field of Classification Search
CPC .. G01J 2003/1213; G01J 3/108; G01J 3/0205; G01J 3/0213; G01J 3/0232; G01J 3/0256
See application file for complete search history.

(56) References Cited

OTHER PUBLICATIONS

Inoue, Takuya, et al., "Realization of narrowband thermal emission with optical nanostructures," Optica, Jan. 14, 2015, vol. 2, No. 1, pp. 27-35.
Liu, Xinyu, et al., "Reconfigurable room temperature metamaterial infrared emitter," Optica, Apr. 13, 2017, vol. 4, No. 4, p. 430-433.

* cited by examiner

METAMATERIAL-BASED IR EMITTER HAVING MODULATABLE EMISSIVITY

The invention relates to a modulatable infrared emitter comprising a heating element, a planar base element, a dielectric interlayer, and a planar cover element which is a structured metamaterial, and an actuator, in which the actuator is configured for a relative movement of the cover element and the base element between a first and a second position in order to modulate the intensity of the emission of the infrared emitter. The invention further relates to production methods for the infrared emitter, methods for the modulated emission of infrared red radiation by means of the infrared emitter, and preferred uses of the infrared emitter. A system comprising the infrared emitter and a control device for regulating the actuator are also preferably the subject matter of the invention.

BACKGROUND AND PRIOR ART

Modulatable infrared emitters (IR emitters) are relevant for a large number of applications in spectroscopy. In particular, the spectroscopy of gases is often carried out with the help of infrared radiation. Electromagnetic radiation in the infrared range triggers vibrations of the gas molecules involved at certain frequencies or wavelengths, which can be detected by absorption lines in the spectrum.

For example, environmental sensors are heavily dependent on optical or spectroscopic systems that work in the mid-infrared range—i.e. at wavelengths from 2 µm to 10 µm—because this is where the infrared bands are for many important substances such as carbon dioxide or methane.

Photoacoustic spectroscopy is often used, in which intensity-modulated infrared radiation is used at frequencies in the absorption spectrum of a molecule to be detected in a gas. If this molecule is present in the beam path, a modulated absorption takes place, which leads to heating and cooling processes, the time scales of which reflect the modulation frequency of the radiation. The heating and cooling processes cause the gas to expand and contract, causing sound waves at the modulation frequency. These can be measured by sound detectors (microphones) or flow sensors.

Photoacoustic spectroscopy allows the detection of the finest concentrations of gases and has a multitude of applications. One example is the detection of $CO_2$, which plays a role in research and climate-control technology. The concentration, for example, of exhaust gases in the air can be measured in this way. Military applications are also relevant in which the smallest concentrations of poison gas can be detected.

Different emitters are used as radiation sources for the applications mentioned, with different advantages and disadvantages. For example, narrow-band laser sources in the infrared range can be used. The laser sources enable the use of high radiation intensities and can be modulated at high frequencies with standard components, for example for photoacoustic spectroscopy. However, the construction is complex and expensive. A corresponding number of lasers must be used, in particular for the detection of different molecules.

It is also known to provide narrow-band thermal emitters based on optical nanostructures. Inoue et al. 2015 discloses a number of different approaches ([8]). The use of metamaterials for selective infrared emitters is discussed with reference to Landy et al. 2008 ([13]). For example, the provision of a single-band and dual-band IR emitter by means of metamaterials is disclosed. In this way, a wavelength-specific transmission with high emissivities and Q-factors can be ensured. In contrast to the laser sources described above, high-frequency modulation of the emitted infrared radiation is not possible.

Thermal, broadband emitters are also known. They have the advantage of a broad spectrum and often lower costs. However, the modulation frequency of these emitters is limited; direct modulation by varying the current supply is slow due to thermal time constants and significantly impairs the service life of the component. Slow modulation often results in a measurement with a poor signal-to-noise ratio due to the inherent noise of the detection components. External modulation through the use of rotating chopper wheels is faster, but the construction is complex and not as compact and robust as would be desirable for many applications. The modulation bandwidths are also limited, and it is difficult to vary the rotational speed of the chopper due to inertia.

At the same time, there is great interest in miniaturizing these IR sensor elements so that they can be integrated into as many technical applications as possible.

Most suitable for miniaturization are sensors or spectrometers the function of which is based on the photoacoustic effect, since this is a method of absorption spectroscopy, and thus significantly shorter optical path lengths are sufficient for a sufficient signal-to-noise ratio, in stark contrast to methods of transmission spectroscopy [7]. At the same time, however, this also requires the availability of miniaturized infrared emitters, which, on the one hand, should achieve the highest possible intensity—since this leads to a direct increase in the measurement signal—but, on the other hand, must also be modulated with the highest possible frequencies. The modulation of the emitter is essential for the photoacoustic effect to occur, since otherwise no acoustic signal is generated in the medium to be examined. At the same time, a higher modulation frequency of the emitter means both an increase in the functional speed of the photoacoustic sensor and an improvement in the signal-to-noise ratio (SNR) [7].

So far, mainly miniaturized thermal IR emitters have been used, so-called microhotplates [5, 6], which are operated at temperatures of a few hundred degrees and reach modulation frequencies of only a few Hz. By using plasmonic structures [8-10], it is possible to positively influence the spectra of such thermal emitters, but the basic problem of high temperatures and low modulation frequencies remains and cannot be solved with the existing technology.

For the production of miniaturized, mechanical-electronic devices, microsystem technology is used in many fields of application today. The microsystems (microelectromechanical system, abbreviated as MEMS) that can be produced in this way are very compact (micrometer range) with excellent functionality and ever lower manufacturing costs. For example, DE 10 2017 206 183 A1 describes fast and compact comb drives as MEMS actuators.

A combination of micro-/nano-electromechanical systems with metamaterials has also already been proposed in some cases, which has enormous potential for the development of novel, tunable components. In this case, the possible areas of application range from areas as diverse as communication and THz technology to medical diagnostics [1-4].

Liu et al. 2017 describe a modulation of the spectral emission of surfaces, which can be used for infrared camouflage or friend-or-foe recognition ([19]). By means of a metamaterial, the detectable emission is changed over a range which corresponds to a temperature change of 20° C. In combination with MEMS actuators, dynamic infrared patterns can be generated on surfaces in order to avoid infrared camera detection or to enable identification of the corresponding objects.

A use of MEMS technology based on metamaterials for modulating a heatable IR emitter which is suitable for use in photoacoustic spectroscopy is unknown in the prior art.

Object of the Invention

The object of the invention is to provide a modulatable infrared emitter and a method for generating modulated infrared radiation which do not have the disadvantages of the prior art. In particular, an object of the invention was to provide a high-frequency and variably modulatable infrared emitter which is characterized at the same time by a simple, inexpensive, compact structure.

SUMMARY OF THE INVENTION

This object is achieved by the features of the independent claims. Preferred embodiments of the invention are specified in the dependent claims.

The invention preferably relates to a modulatable infrared emitter comprising
 a heating element
 a planar base element made of a conductive material
 a dielectric interlayer
 a planar cover element made of a conductive material and
 an actuator
in which the cover element is a structured metamaterial with periodically arranged unit cells and the actuator is configured for relative movement of the cover element and the base element between a first and second position in order to modulate the intensity of the emission of the infrared emitter.

The actuator can be used to modulate the intensity of the emitted infrared radiation in a particularly quick and simple manner. In contrast to known intensity modulations in infrared emitters by varying the current supply, the modulation according to the invention is not limited by thermal time constants. Rather, for example, MEMS actuators can be used to achieve modulation frequencies of well over 100 Hz up to 100 kHz. Such modulation frequencies are particularly advantageous for photoacoustic spectroscopy. However, the modulatable infrared emitter is also suitable for any application in which fast and reliable modulation of infrared radiation is required.

As explained in detail below, the modulation of the emission of the infrared radiation is based on the utilization of the properties of the structured metamaterial of the cover element. In the second position, the cover element made of the structured metamaterial is preferably located at a distance that is as close as possible, limited only by the dielectric interlayer, with the greatest possible degree of overlap above the base element. In this second (resonant) position, infrared radiation can couple to the layer system comprising the cover element, dielectric interlayer, and base element, so that a particularly high emissivity occurs or an infrared emission with high intensity occurs at a preferred infrared resonance wavelength.

In the first position, there is preferably no resonant coupling, so that the IR emitter has a significantly reduced emissivity at the resonance wavelength or an infrared emission takes place with a significantly reduced intensity. With regard to the resonance wavelength, the intensity of the emission of the infrared radiation can be quickly and reliably modulated by means of a position change between a resonant state (second position) and a non-resonant state (first position) provided by the actuator.

For this purpose, for example, the actuator can be configured in such a way that it lowers the vertical distance between the cover element and the base element from a first, non-resonant position to a second, resonant position. It is also possible for the actuator to displace the base element and cover element horizontally with respect to one another, with resonant emission taking place in the case of sufficient overlap in a second position. This fast and reliable modulation capability clearly distinguishes the IR emitter from known infrared emitters of the prior art.

In the context of the invention, a modulatable infrared emitter preferably characterizes a device which emits electromagnetic radiation. This radiation preferably has a wavelength range in the infrared (IR) range, in particular between approximately 700 nanometers (nm) and 1 millimeter (mm) wavelength. The corresponding frequency of the emitted radiation can be in the range between approximately 300 gigahertz (GHz) and 400 terahertz (THz). The spectrum can also preferably be reproduced using the wave number $m^{-1}$ or $cm^{-1}$, as is customary in the field of spectroscopy. One skilled in the art knows how to convert these units.

The spectrum is selected in particular so that it corresponds to the preferred field of application of the emitter, namely infrared spectroscopy and in particular photoacoustic spectroscopy. In particular, the vibrational excitation of the gas molecules subject to spectroscopy and/or detection is preferred, which correspond to a preferred spectral range depending on the gas molecules. For example, a spectral range of around 2.4 micrometers ($\mu m$) is suitable for the excitation of $CO_2$ molecules. Particularly preferred wavelength ranges of the infrared radiation are 700 nm to 10 $\mu m$, preferably 1 to 10 $\mu m$, particularly preferably 2 $\mu m$ to 10 $\mu m$.

The IR emitter preferably emits a beam which is oriented in a preferred direction in the form of a straight line. The orientation of the beam is preferably specified by the surface normal to the base element, the dielectric interlayer, and the cover element, which are excited to infrared radiation by the heating element. In the following, the term beam is intended to describe the preferably bundled part of the radiation along the preferred beam direction of the emitter, which is emitted by the emitter, in particular the areas of greatest intensity along this direction defining the beam. Intensity is preferably defined as the surface power density and preferably has the unit watts per square meter or $W/m^2$ for short.

The structure of the modulatable infrared emitter defines a preferred direction of emission of an infrared beam along the surface normal of the layer structure on the heating element. However, additional components such as, e.g., lenses may be integrated into the emitter or attached externally, which ensure a bundling or collimation of the beam. One skilled in the art knows how to form the emission profile of the radiation source through the design of the IR emitter and through the use of further components so that a desired beam profile and a desired beam direction result. The modulatable IR emitter can preferably manage without additional lenses or be present as a system comprising a radiation source and at least one lens for collimating the beam.

The emitter can be modulated, which means that the intensity of the emitted radiation, preferably the intensity of the beam, can be changed in a controllable manner over time. The modulation should preferably bring about a change in the intensity over time as a measurable variable. That means, for example, that the intensity over time between the weakest intensity measured within the measurement period and the strongest intensity measured within the same period of time is greater than the sensitivity of a device typically used for the radiation spectrum and the application to measure or determine the intensity. The difference between the strongest and the weakest adjustable intensity is preferably significantly greater than a factor of 2, more preferably 4, 6, or 8. It is particularly preferable for the intensity of the modulated beam to be modulated for one or more predetermined resonance wavelengths. A modulatable infrared emitter has a variety of uses. Any form of infrared spectroscopy and, in particular, photoacoustic spectroscopy should be mentioned as a relevant application.

In order to generate the infrared radiation, thermal energy is provided in the form of a heating element. A micro-heating element is particularly preferred. A micro-heating element is preferably understood to mean a heating element with dimensions in the micrometer range (μm). The heating element comprises a heatable layer made of a conductive material which produces Joule heat when an electrical current flows through it. The heat produced preferably shows a dependency on the ohmic resistance of the element and on the square of the current strength or on the square of the applied voltage and the inverse ohmic resistance, depending on whether a current or a voltage source is used.

In a state of equilibrium, the heat produced is equal to the heat losses through heat conduction, convection, and heat radiation (synonymous with thermal radiation, infrared radiation) which is emitted on the outer boundary surfaces of the heatable layer through which current flows. As is known to one skilled in the art, the heat produced causes, inter alia, thermal radiation, in particular through the thermal movement of particles which results, for example, in an acceleration of charge carriers and/or oscillating dipole moments. In this way, infrared radiation can be generated in a targeted manner by a heatable layer through which current flows. The heatable layer is preferably made of metal, for example tungsten or platinum. By applying a suitable voltage and the resulting current flow, Joule heat and thus ultimately infrared radiation is generated.

The radiation spectrum of a heating body can be preferably approximated by Planck's law of radiation, in which the differences between a real heatable layer and a black body are known to one skilled in the art, for example the emissivity or the real deviation from a thermal equilibrium of the body. Despite these deviations, the generated spectrum and its intensity are essentially described by the temperature and the radiating surface in accordance with Planck's law of radiation.

One skilled in the art can thus achieve a preferred spectrum with a preferred intensity distribution through the targeted design of the micro-heating element. For this purpose, in addition to the material and the geometric design of the heating element, the electrical energy provided and the extent of the heat losses of the heating element are preferably decisive, in addition to the thermal radiation. The extent of these heat losses is determined, for example, by the thermal conductivity between the heating element and the adjacent materials and/or fluids as well as their thermal capacity and the size of the boundary surface(s).

The micro-heating element is preferably at least partially free-standing and enables, for example, thermal expansions within the IR emitter due to strong temperature changes and translational movements. Partially free-standing means that it is at least partially not frictionally and/or positively connected to other elements of the emitter at the boundary surfaces and therefore has a degree of freedom of movement in a direction essentially perpendicular to the boundary surface.

The infrared emitter according to the invention is characterized in that the heating element has a planar base element, a dielectric interlayer, and a planar cover element made of a metamaterial.

Planar preferably means a dimensioning in which the thickness of the base element or cover element is significantly less than its length and/or width. For example, the term planar can mean a thickness of less than 1500 nm or preferably less than 500 nm, with the elements having a length or width in the range of hundreds of micrometers or several millimeters, so that a ratio between the thickness and the length or width of the base element or cover element of more than 1:10, more than 1:50, or more than 1:100 is preferred.

The shape of the base element, the dielectric interlayer, or the cover element can be, for example, rectangular, square, or circular. Preferably, however, the base element, dielectric interlayer, or cover element have essentially the same shapes and essentially the same surface areas.

As explained in detail below, the layer structure that can be moved by the actuator, which consists of the base element, dielectric interlayer, and cover element on the heating element, has a decisive influence on the intensity of the emitted infrared radiation.

While there is a resonant emission of infrared radiation (the emissivity in relation to a resonance wavelength is particularly high) in a second position, a first relative positioning of the base element and cover element is chosen so that there is no resonant IR emission or only a significantly reduced IR emission.

The modulation of the emissivity by the actuator is thus based on an electromagnetic resonance for the emission of the infrared radiation, which occurs in the second relative position of the cover element and the base element as opposed to the first position. In the second position, the cover element made of the structured metamaterial is preferably located at a distance that is as close as possible, limited only by the dielectric interlayer, with the greatest possible degree of overlap above the base element.

In the second position, the IR emitter is preferably characterized by a structure in which the base element made of a conductive material is separated from an overlying cover element made of a structured metamaterial essentially only by the dielectric interlayer, and in which the cover element covers the surface of the base element to a preferably maximum proportion.

With a suitable choice of the metamaterial, such a layer structure composed of the base element, dielectric interlayer, and cover element preferably forms a metamaterial perfect absorber or at least an absorber which comes very close to a metamaterial perfect absorber. A metamaterial perfect absorber is characterized in that incident electromagnetic radiation is almost completely absorbed, i.e. has an absorption of almost 1 in relation to at least one resonance wavelength.

Due to Kirchhoff's law of radiation, such a layer structure advantageously also functions as an almost perfect IR emitter in the context of the structure of the IR emitter according to the invention. Kirchoff's law of radiation states that for all bodies in thermal equilibrium at a given temperature, the ratio between emission and absorption A for radiation of the same wavelength is constant and the amount is equal to the specific radiation of the black body at this temperature. In other words, a material with a high degree of absorption for a certain wavelength will also have a high emissivity for the wavelength.

The cover element made of metamaterial, the dielectric layer, and the base element can be selected such that a resonant absorption occurs at at least one preferred infrared wavelength in the second position. In this position, the IR emitter will emit the thermal energy provided by the heating element in a resonant manner at at least that resonance wavelength. The first position can advantageously be chosen so that the resonance does not occur and the IR emitter has only a low emissivity over a broad infrared spectrum.

With regard to the resonance wavelength, the emissivity can be quickly and reliably modulated by means of a position change between a resonant state (second position) and a non-resonant state (first position) provided by the actuator. As explained in more detail below, it is possible, for example, to achieve modulation frequencies of several kHz with MEMS actuators. The combination of a movable cover element made of a structured metamaterial and a base element that can be heated by a heating element therefore enables the provision of a high-frequency IR emitter with a high modulation depth.

This advantageously results in an excellent signal-to-noise ratio at high speeds for applications in photoacoustic spectroscopy. While the speed of known modulatable IR emitters is limited by the modulation frequency of the IR emitter, the physical upper limit is preferably only stipulated by the relaxation times of the electrons in the gas being examined with the high-frequency modulatable IR emitter described.

The choice of one or more resonance wavelengths can be made through a suitable choice of a structured metamaterial.

For the purposes of the invention, the terms "structured metamaterial" or "metamaterial" are preferably used synonymously and characterize an artificially produced structure, the permeability of which to electrical and magnetic fields, i.e. its electrical permittivity ($\varepsilon(w)$) or magnetic permeability ($\mu(w)$), can be set dependent on the frequency and based on the application. In particular, structured metamaterials can thus have electromagnetic properties that are not found in natural materials. For example, it was shown as early as 1968 that metamaterials can reach a negative refractive index [11].

The structured metamaterial is preferably formed from an array of periodic unit cells, the dimensions of which are smaller than the wavelength of the electromagnetic radiation which is to be influenced in the desired manner by the metamaterial. Similarly to the known unit cells of a crystal, a "unit cell" or "elementary cell" is preferably understood to be a smallest geometric unit of the structured metamaterial which is repeated periodically in the planar plane of the metamaterial. A two-dimensional, periodic arrangement of all unit cells preferably forms the surface of the structured metamaterial.

Highly conductive metals such as gold, silver, or copper, which can be arranged, for example, as split-ring resonators, are particularly suitable as materials for the metamaterial [12].

Such resonators are also particularly suitable for forming a metamaterial perfect absorber. For example, as described by Landy et al., a metamaterial perfect absorber can be formed from two metallic layers, which are separated by a dielectric interlayer. The upper metal layer can have several so-called electric ring resonators (EER), while the lower metal layer is formed by a homogeneous strip [13]. With such a structure, there is an electrical coupling with the upper metal layer and a magnetic coupling with anti-parallel currents in both layers and a Lorentz-like magnetic response. A resonance in the microwave range is realized in the original structure. By appropriately dimensioning the unit cell, a resonance of the absorptions in the infrared range can also be achieved [14].

One skilled in the art knows various preferred forms of metamaterials and structures for metamaterial perfect absorbers which are suitable for forming a resonant absorption at a desired wavelength [15]. For example, a hexagonal array of circular structures can also be used as a metamaterial above a homogeneous base plate [16]. Rectangular or cross-shaped resonators can also preferably be used for a metamaterial perfect absorber within the context of the invention.

As explained in detail below, the structured metamaterial, the dielectric interlayer, and the base element are preferably designed in such a way that a resonant emission occurs at a resonant wavelength in the infrared range, preferably in a wavelength range of 1 µm to 10 µm, preferably 2 µm to 10 µm.

In addition to the described preferred embodiments for a cover element made of a metamaterial, base element, and a dielectric interlayer, one skilled in the art can also find further suitable structuring, dimensioning, and/or materials on the basis of numerical simulation. The electromagnetic theory and systems of equations for numerical solutions are known to such a person [15].

The layer system made up of the base element, dielectric interlayer, and cover element is preferably selected in such a way that a particularly high emissivity is achieved in the second (resonant) position for a desired resonance wavelength.

For a metamaterial perfect absorber, the energy balance can be summarized as follows: $T(\omega)+R(\omega)+A(\omega)=1$, where T is transmission, R is reflection, and A is absorption. The parameters of the cover element, the base element, and the dielectric interlayer are preferably selected so that $A(\omega)$ is maximized in the second position, whereby, according to Kirchhoff's law, a resonant emission also occurs at the frequency $\omega$, and the emissivity is maximized.

The emissivity of a body preferably indicates how much radiation a body emits compared to an ideal heat radiator, a black body. In the second position, when there is an almost perfect absorber on the heating element, a particularly high emissivity of theoretically up to 1 can be achieved.

In a preferred embodiment, the modulatable infrared emitter is characterized in that the unit cell of the structured metamaterial comprises a resonator which is formed by bracing the conductive material, the resonator preferably being in the form of a split ring resonator (SRR), electric ring resonator (ERR), a cross, a square, a circle, a hexagon, and/or combinations of these shapes.

A resonator preferably characterizes a structure made of braces of a conductive material, which can couple to an electric field. In particular, the aforementioned forms of resonators in the form of split ring resonators (SRR), electric ring resonators (ERR), crosses, squares, circles, and/or hexagons are particularly suitable for coupling to the electric field of infrared radiation. However, other forms of electrical resonators can also be preferred in order to achieve the desired resonant emission. Such shapes are known to one skilled in the art, for example, from US 2013/0314765 A1, one skilled in the art knowing how to adapt the dimensioning in order to achieve a resonance at a desired wavelength, preferably in the range of from 1 µm to 10 µm, preferably 2 µm to 10 µm.

In a preferred embodiment, the unit cells form a two-dimensional periodic lattice, the lattice angle being between 60° and 120°, preferably 90°, and the two lattice constants being between 5% and 40%, preferably 10% and 25%, of a resonance wavelength, in which the resonance wavelength is selected from a range between 1 µm to 10 µm, preferably 2 µm to 10 µm.

The preferred dimensioning of the unit cells is thus based on the desired resonance wavelength at which there is a high emissivity and an emission with particularly high intensity.

For the particularly preferred resonance wavelengths in a range between 2 µm to 10 µm, preferred lattice constants are in a range between 100 nm and 4 µm, particularly preferably 200 nm and 2.5 µm. Intermediate ranges from the aforementioned ranges can also be preferred, such as 100 nm to 200 nm, 200 nm to 300 nm, 300 nm to 400 nm, 400 nm to 500 nm, 600 nm to 700 nm, 700 nm to 800 nm, 800 nm to 900 nm, 900 nm to 1000 nm, 1000 to 1100 nm, 1100 to 1200 nm, 1300 to 1400 nm, 1400 nm to 1500 nm, 1600 nm to 1700 nm, 1700 nm to 1800 nm, 1800 nm to 1900 nm, 1900 nm up to 2000 nm, 2000 nm to 2100 nm, 2100 nm to 2200 nm, 2200 nm to 2300 nm, 2300 nm to 2400 nm, 2400 to 2500 nm, 2600 to 2700 nm, 2700 to 2800 nm, 2800 nm to 2900 nm, 2900 nm to 3000 nm, 3000 to 3100 nm, 3100 to 3200 nm, 3300 to 3400 nm, 3400 nm to 3500 nm, 3600 nm to 3700 nm, 3700 nm to 3800 nm, 3800 nm to 3900 nm, 3900 nm to 4000 nm. One skilled in the art recognizes that the aforementioned range limits can also be combined in order to obtain further preferred ranges, such as, for example, 200 nm to 800 nm, 1000 nm to 1500 µm, or even 1400 nm to 2500 nm.

The terms lattice angle and lattice constants are preferably understood to mean the usual lattice parameters for describing a (two-dimensional) lattice. As is known, a two-dimensional lattice can be generated by periodically shifting a unit cell by the same distance in each case in two specific spatial directions, i.e. along two lattice vectors. The lattice angle preferably corresponds to the angle between the two lattice vectors, while the lattice constants characterize the length of unit cells in the two dimensions or the distance between two unit cells along the direction of displacement.

The lattice angles and lattice constants mentioned have proven to be particularly advantageous for the formation of an electromagnetic resonant emission of the IR radiation at wavelengths in the range of from 1 µm to 10 µm, preferably 2 µm to 10 µm.

The embodiment is therefore particularly suitable for use in infrared spectroscopy, in particular for photoacoustic spectroscopy.

The choice of the lattice constant depends preferably on the desired resonance wavelength. For preferred resonance wavelengths in a range between 2 µm and 3 µm, preferred lattice constants are in a range, for example, between 100 nm and 1.2 µm, especially preferably 200 nm and 750 nm.

Both lattice constants are particularly preferably essentially the same, so that a particularly high emissivity can be achieved at a specific resonance wavelength.

However, it can also be preferred to choose different lattice constants in the different spatial directions. This advantageously makes it possible to provide a modulatable IR emitter which, in the second (resonant) position, has IR radiation with a high emissivity in a range of at least two resonance wavelengths.

In this way, the modulatable IR emitter can advantageously simultaneously provide IR radiation for photoacoustic spectroscopy of two or more gases. A first resonance wavelength can be, for example, approximately 2.4 µm in order to detect $CO_2$, while a second resonance wavelength can be approximately 3 µm in order to detect methane, for example.

In particular for spectroscopic applications, such as photoacoustic spectroscopy for the detection of gas molecules, the use according to the invention of a metamaterial in an IR emitter opens up diverse application possibilities with high economic relevance.

In a preferred embodiment, the cover element is made from a metal, particularly preferably from gold, silver, aluminum, tungsten, molybdenum, titanium, and/or copper.

In a further preferred embodiment, the base element is made from a metal, particularly preferably from gold, silver, aluminum, tungsten, molybdenum, titanium, and/or copper.

The cover element and the base element are particularly preferably made from a material which has essentially the same electrical conductivity.

Terms such as essentially, approximately, about, etc. preferably describe a tolerance range of less than ±20%, preferably less than ±10%, even more preferably less than ±5%, and in particular less than ±1%. Statements such as essentially, approximately, about, etc. disclose and always also include the exact stated value.

In a further preferred embodiment, the base element and the cover element are made from the same material.

In a further preferred embodiment, the dielectric interlayer is made from a material selected from a group comprising aluminum nitride, silicon nitride, aluminum oxide, silicon oxide, titanium dioxide ($TiO_2$), and/or tantalum oxide ($Ta_2O_5$).

For the aforementioned choice of materials for the base element, the dielectric interlayer, and the cover element in the form of a structured metamaterial, there is particularly good tuning, preferably a particularly good magnetic coupling, so that high electromagnetic resonances and IR emissions are achieved in the second position. In addition, the materials are characterized by high resistance to corrosion, oxidation, or mechanical influences, so that a long-lasting, robust IR emitter is guaranteed.

In a preferred embodiment, the base element is a continuous conductive layer. This reduces the reflections subject to losses and achieves particularly good impedance adaptation between the cover element and the base element.

In a further preferred embodiment, the base element, the dielectric interlayer, and the cover element are made from CMOS-compatible materials. As a result, the modulatable IR emitter can be manufactured on a single chip by means of CMOS circuitry. By means of the possible integration of CMOS technology, highly miniaturized and powerful, modulatable IR emitters can be provided. In addition, the CMOS technology enables cost-effective mass production, which ensures a commercially attractive product. Preferred materials and manufacturing steps for using CMOS technology to manufacture MEMS devices are known to one skilled in the art, for example from Qu et al. [17].

In a further preferred embodiment, the cover element has a layer thickness between 100 nm and 1500 nm. Preferred layer thicknesses are in the aforementioned range, with intermediate ranges also being preferred, such as, for example, 100 nm to 200 nm, 200 nm to 300 nm, 300 nm to 400 nm, 400 nm to 500 nm, 600 nm to 700 nm, 700 nm to 800 nm, 800 nm to 900 nm, 900 nm to 1000 nm, 1000 to 1100 nm, 1100 to 1200 nm, 1300 to 1400 nm, or even 1400 nm to 1500 nm. One skilled in the art recognizes that the aforementioned range limits can also be combined in order to obtain further preferred ranges, such as, for example, 100 nm to 500 nm, 400 nm to 1000 nm, or even 800 nm to 1500 nm.

In a further preferred embodiment, the dielectric interlayer has a layer thickness between 100 nm and 1500 nm. Preferred layer thicknesses are in the aforementioned range, with intermediate ranges also being preferred, such as, for example, 100 nm to 200 nm, 200 nm to 300 nm, 300 nm to 400 nm, 400 nm to 500 nm, 600 nm to 700 nm, 700 nm to 800 nm, 800 nm to 900 nm, 900 nm to 1000 nm, 1000 to 1100 nm, 1100 to 1200 nm, 1300 to 1400 nm, or even 1400 nm to 1500 nm. One skilled in the art recognizes that the aforementioned range limits can also be combined in order to obtain further preferred ranges, such as, for example, 200 nm to 600 nm, 300 nm to 1000 nm, or even 700 nm to 1500 nm.

In a further preferred embodiment, the base element has a layer thickness between 100 nm and 1500 nm. Preferred layer thicknesses are in the aforementioned range, with intermediate ranges also being preferred, such as, for example, 100 nm to 200 nm, 200 nm to 300 nm, 300 nm to 400 nm, 400 nm to 500 nm, 600 nm to 700 nm, 700 nm to 800 nm, 800 nm to 900 nm, 900 nm to 1000 nm, 1000 to 1100 nm, 1100 to 1200 nm, 1300 to 1400 nm, or even 1400 nm to 1500 nm. One skilled in the art recognizes that the aforementioned range limits can also be combined in order to obtain further preferred ranges, such as, for example, 100 nm to 400 nm, 400 nm to 1200 nm, or even 700 nm to 1400 nm.

The aforementioned layer thicknesses are particularly suitable for providing an almost perfect metamaterial absorber in the second resonant position, which absorber forms an almost perfect IR emitter when heated by the heating element.

The aforementioned preferred embodiments of the structuring of the metamaterial, as well as the layer thicknesses and choice of materials, are particularly suitable for ensuring a high emissivity and radiation with high intensity in a (second) resonant position. While theoretically emissivities of up to 1 are possible using a nearly perfect metamaterial absorber, production tolerances or energy losses in practice lead to lower maximum emissivities in the resonant position.

Advantageously, a high modulation depth can also be achieved with emissivities of significantly less than 1 in the (second) resonant position. The modulation depth of the modulatable IR emitter is preferably influenced by the difference in the emissivity in a second position compared to the first position. In other words, not only the maximum possible emissivity in the second (resonant) position is decisive for the possible modulation depth of the IR emitter, but also the lower emissivity, which is preferably lower in the first (non-resonant) position.

The inventors have recognized that the vertical distance between the base element and the cover element and their degree of overlap are suitable for setting the emissivity in a first (resonant) position and in a second (non-resonant) position.

In a preferred embodiment, the actuator is therefore configured for a vertical translational movement of the cover element and/or the base element along the direction of emission of the infrared emitter, which changes the distance between the cover element and the base element. The distance in the second position is preferably less than it is in the first position.

The cover element and the base element are preferably arranged one above the other in two parallel planes. In a first position, the actuator preferably keeps the cover element and/or base element a sufficiently vertical distance away, which prevents electromagnetic resonance and the formation of a metamaterial perfect absorber. Only through a preferred reduction in the distance through a vertical translational movement, that is to say, for example, lowering the cover element onto the dielectric interlayer, does a high emissivity and resonant radiation occur in a second position.

In a preferred embodiment, the cover element is at a distance of at least 500 nm from the dielectric layer in the first position, preferably at least 1000 nm, and it is a distance of at most 200 nm from the dielectric layer in the second position, preferably at most 50 nm, especially preferably 0 nm.

The aforementioned distances have proven to be particularly advantageous in order to ensure a significantly reduced emission in the first position in contrast to the second position. A vertical distance of 0 nm between the cover element and the dielectric layer preferably characterizes a contact between the cover element and the dielectric layer. It is known to one skilled in the art that an actual distance of more than 0 nm can be present even with direct contact due to the roughness of the two contacting surfaces. Such deviations are covered by the disclosed embodiment.

The inventors have also recognized that, in addition to a variation in the distance through a vertical translation movement, a relative horizontal translation of the cover element and base element can also be used to vary the emissivity and therefore the intensity of the infrared radiation.

In a preferred embodiment, the actuator is configured for a horizontal translational movement of the cover element and/or the base element orthogonally as relates to the direction of emission of the infrared emitter, which changes the degree of overlap between the cover element and the base element. There is preferably a lower degree of overlap in the first position than in the second position.

The degree of overlap is preferably understood to mean the ratio of the surface of the base element, over which a section of the cover element is located in the emission direction, to the total area of the base element.

A degree of overlap of 0% thus characterizes a state in which there is no section of the cover element made of structured metamaterial above the base element in the emission direction. With a degree of overlap of 0%, there is no resonant emission of the IR radiation.

A degree of overlap of 100%, however, characterizes a relative position or a state in which a section of the cover element made of structured metamaterial is located above the entire surface of the base element in the emission direction. With a degree of overlap of 100%, a resonant emission of the IR radiation takes place essentially over the entire surface of the base element. With a degree of overlap between 0 and 100%, resonant emission preferably occurs only over the covered portion of the base element.

Advantageously, the emissivity or the intensity of the emitted IR beam can thus also be precisely modulated by a horizontal translational movement and a variation in the degree of overlap.

In a preferred embodiment of the invention, the cover element and base element have a degree of overlap in the first position of less than 40%, preferably less than 10%, particularly preferably 0%, while the cover element and base element have a degree of overlap in the second position of more than 40%, preferably more than 80%, especially preferably 100%.

The mentioned degrees of overlap can be implemented mechanically very well and ensure sufficient modulation depths of the IR emitter.

With a horizontal translational movement of the cover element relative to the base element in order to change the degree of overlap, the actuator is preferably configured such that the vertical distance in the second position is preferably less than 200 nm, especially preferably less than 100 nm, more preferably 0 nm. For this purpose, a horizontal translational movement can take place without an additional vertical translational movement. However, it can also be preferred that a horizontal translational movement is overlapped by a vertical translational movement.

For the purposes of the invention, vertical preferably characterizes the emission direction of the IR emitter, which is given by the surface normal as relates to the cover element and base element. Whereas horizontal preferably means a direction in a plane which is parallel to the planes in which the cover and base elements are arranged. Designations such as one above the other, overlapping, etc. are based on the vertical direction, i.e. the direction of emission of the IR emitter. This can, but does not have to, coincide with a gravitational direction.

An actuator is used to ensure the relative movement of the base and cover element. An actuator preferably converts, in particular, an electrical control signal into a movement. It can be a MEMS actuator which, for example, is an electrostatic actuator.

The ratio between the maximum and minimum intensity of the emitted IR radiation that can be set by the relative movement can be referred to as the extinction ratio. It can be determined directly from the ratio between maximum intensity and minimum intensity and preferably indicated directly by this ratio. However, it can also be preferred that this ratio is expressed in the logarithmic scale of decibels (dB) as is customary, for example, in communications engineering. One skilled in the art understands that the greater the extinction ratio, the greater the difference between the emissivities that can be set in the first and second position.

The maximum modulation frequencies achievable at the desired modulation depths should preferably be at least 1 kilohertz (kHz), especially preferably at least 10 kHz, more preferably at least 20 kHz, very especially preferably at least 30 kHz, and in particular at least 100 kHz. It is particularly preferred to achieve modulation frequencies in the range of audible sound and/or ultrasound for an application in photoacoustic spectroscopy. The modulation bandwidth over which the desired modulation depth is achieved preferably relates to the entire frequency range from 0 Hz to the maximum modulation frequency.

The desired modulation can preferably be expressed in a corresponding temporal profile of the emitted radiation intensity. In order to determine the feasibility of such a desired intensity profile over time, the modulation depth and the bandwidth over which this modulation depth can essentially be achieved are of particular importance. The resolution of an electronic control of the IR emitter is also preferably relevant for the feasibility. In this case, it may be significant which different intensity levels can be achieved between minimum and maximum intensity with which frequency.

It is preferred that the IR emitter has an electrical control with which the relative movement of the base element and cover element caused by the at least one actuator is regulated. Such a control can be implemented, for example, via a control device. The desired spectra, intensities, and modulations can be set by means of a control.

Control preferably means that electrical control signals are transmitted directly to the actuator and the heating element, which result in the desired radiation properties. In this way, in particular, a specific temperature and/or a specific temperature profile can be set for the heating element. In addition, a certain modulation signal can be achieved through the relative movement triggered by the actuator (possibly in coordination with a temperature profile). It is typically an analog signal that is generated by a control device. This device can, in turn, preferably receive a suitable, digital, electronic signal, for example by means of a control computer, which is then advantageously converted into suitable control signals by the control device.

It is particularly preferred that large portions of the IR emitter have dimensions in the micrometer range in order to enable a miniaturized structure.

In a preferred embodiment, the heating element is a micro-heating element.

In a preferred embodiment, the actuator is a MEMS actuator, preferably selected from the group comprising an electrostatic actuator, a piezoelectric actuator, an electromagnetic actuator, and/or a thermal actuator.

A MEMS actuator is preferably an actuator which is produced with the aid of conventional production methods of microsystem technology and which also advantageously has dimensions in the µm range. Such an actuator is particularly compact, robust, and low-maintenance and can be produced simply and inexpensively. In particular, large portions of the emitter can be MEMS elements, that is to say elements with the preferred properties mentioned above, and can be produced in one production step with the MEMS actuator. Desirably, portions of the same substrate can be used for production. This simplifies production and makes it cheaper.

The aforementioned actuators are particularly well-suited for a large number of rapid translational movements and have a low energy requirement, in particular due to their compact design. The range of translational speeds that can be achieved is also very high due to the compact design, low inertia, and linear movement.

In a further preferred embodiment of the modulatable infrared emitter, the MEMS actuator is an electrostatic actuator in the form of a comb drive based on a variation of the comb overlap and/or the comb spacing. MEMS comb drives are known from the prior art, e.g., from patent application DE 10 2017 206 183 A1. In this case, the comb overlap and/or the comb spacing can be varied depending on the embodiment. Because of their dimensions and the movements that can be generated, it has been shown that such MEMS comb drives are particularly suitable for a preferred translational movement and a compact IR emitter.

In a further preferred embodiment, the actuator is coupled to the cover element and configured for a translational movement of the cover element with respect to the base element. A translational movement particularly characterizes a displacement of the cover element or base element. This should preferably take place vertically along the emission direction. Coupled means, in particular, that there is a direct mechanical connection between the cover element and at least one movable element of the actuator, so that a movement of the movable actuator element triggers a movement of the cover element in the desired direction.

The actuator and cover element can preferably be connected directly to one another. It can even be preferred that both the actuator and the cover element comprise the same substrate and/or are made therefrom. In this case, there may be a thermal and/or electrical coupling to the actuator in addition to a mechanical coupling.

However, it may likewise be preferred that the actuator is coupled to the base element and configured for a translational movement of the base element with respect to the cover element. If the base element is firmly connected to a dielectric layer, the actuator can also be connected to the base element indirectly via the dielectric interlayer.

As explained in more detail above, particularly a change in the vertical distance between the cover and base elements or their degree of overlap can be used for modulating the IR radiation. In this regard, both elements are therefore suitable for a translational movement.

Nevertheless, it is particularly preferred that the heating element, the base element, and the dielectric layer are mechanically coupled, and the cover element is moved by means of the actuator. As a result, the IR emitter can be produced particularly efficiently, on the one hand, and the low weight of the cover element enables fast and precise translational movements, on the other hand.

In a preferred embodiment, there is a spacing frame on the dielectric interlayer, the height of which defines the vertical distance between the dielectric interlayer and the cover element. The spacing frame preferably extends along the outer border of the dielectric interlayer, the inner course of the circumference of the spacing frame being greater than the outer circumference of the planar cover element. The at least one actuator preferably connects the spacing frame to the cover element so that, for example, in a first position, the cover element is held at the level of the upper end of the spacing frame, and the actuator is configured for a vertical lowering movement of the cover element as relates to the dielectric interlayer.

In this embodiment, the heating element, the base element, and the dielectric interlayer are preferably stationary, the relative movement between them and the cover element being realized by a translational movement of the cover element and the movement being triggered by the actuator. In this case, a translational movement preferably characterizes a vertical or horizontal displacement of the cover element.

The actuator and spacing frame in this case can preferably be connected directly to one another. It can even be preferred that both the spacing frame and the actuator comprise the same substrate and/or are made therefrom.

In a preferred embodiment, the infrared emitter comprises at least four MEMS actuators, which are installed on the outer sides of the cover element and are configured to control the relative movement of the cover element and the base element between the first and second position simultaneously. A particularly uniform and rapid translation of the cover element can be ensured by using at least four MEMS actuators, which may be located on the outer sides of the cover element.

As previously described, the several MEMS actuators can particularly preferably be attached to a spacing frame, which is preferably applied as a border on the dielectric interlayer and the height of which defines the vertical distance from the cover element to the dielectric interlayer in the first position.

The preferred number of MEMS actuators can be based on the shape of the cover element. In the case of a planar, rectangular cover element and a rectangular spacing frame with a correspondingly larger border, at least four MEMS actuators are preferred, with one MEMS actuator being installed on each side. In the case of a hexagonal cover element, accordingly six MEMS actuators can preferably be used, while in the case of a triangular shape, three MEMS actuators may also be preferred. Integer multiples of the respective number of MEMS actuators are also preferred in order, for example, to attach 2, 3, or more MEMS actuators to each outer side of the cover element.

In a further preferred embodiment, the infrared emitter has a housing in which the heating element, the base element, the dielectric interlayer, the cover element, and the actuator are installed.

The housing can preferably be based on the dimensions and shapes of the installed elements. It may also be preferred that the housing be significantly larger than the installed elements in order to improve the manageability of the emitter and provide a robust device.

For example, the heating element, actuator, base element, dielectric interlayer, and/or cover element can be MEMS elements and/or have dimensions in the (sub)micrometer range, the housing having dimensions in the centimeter range.

It is preferred that the housing has a contiguous outer surface and is closed to the inside. In particular, the heating element is installed in the interior of the housing. As a result, it can be protected from external influences, and emission of the IR radiation to the outside can be avoided except in the preferred emission direction.

It is preferred that the micro-heating element is not thermally insulated from the housing, but rather that a non-radiative heat emission from the heating element to the housing is possible, so that heat can flow away from the heating element. Thus, for example, a desired equilibrium can be established between the heat generated by the current-carrying, heatable layer made of conductive material and the heat discharged to the environment by the heating element, the desired radiation properties are generated, and/or the desired modulation properties are achieved.

For example, it may be preferred that the housing and/or micro-heating elements are made of the same material and that there is sufficient heat conduction between directly connected elements.

The housing can preferably have a heat sink for its own heat dissipation.

It may be desirable to thermally decouple certain elements, such as the cover element, from the housing. This preferably means that the cover element does not heat up significantly due to the use of at least one suitable material at a connection point (for example a small connection surface and/or suitable thickness of the connection) or due to a suitable design.

A suitable material at the connection point preferably comprises the entire connection surface. Suitable materials relate, in particular, to the thermal conductivity of the materials, expressed in watts per meter and Kelvin (W/m·K). Preferred thermal conductivities at the connection point are less than 10 W/m·K, especially preferably less than 1 W/m·K, and in particular less than 0.1 W/m·K.

For example, an oxide layer can be preferred. So that the direct transfer of heat between the micro-heating element and the screen structure is minimized, it can be preferred that the housing is configured to generate a vacuum inside. A vacuum preferably characterizes a pressure of less than $30 \times 10^3$ Pascal (Pa), especially preferably of less than 100 Pa, and in particular of 0.1 Pa and less. Configured means that the housing is designed to be sufficiently pressure-tight.

Due to the resonant emission behavior of the IR emitter in the second position, there is already an IR emission with narrower frequency spectra around one or more resonance wavelengths. Depending on the use of the IR emitter, e.g. with different spectroscopy methods, however, it may be desirable to use even narrower spectra. In addition, particularly in the first position, there is a transmission over a broader frequency spectrum, albeit with a low intensity.

Frequency filters can preferably be used to select especially narrow-band spectra and to minimize IR emission outside the desired narrow-band spectra. These frequency filters are preferably integrated into a housing.

The filters used can advantageously have different filter properties, for example bandpass filters, shortpass filters, longpass filters, notch filters, and any combination of these filters that lead to the desired spectral influences can be used. The frequencies or frequency ranges in which the filters function can be selected as required depending on the application. A filter wheel, for example, can be used as the filter, with different filter properties being installed on the filter. The desired filter can be selected mechanically by turning the filter wheel. The filter wheel can preferably be rotated by an electric drive.

The use of a Fabry-Perot filter is also conceivable. Such a filter can be used, for example, to select very narrow spectra. The Fabry-Perot interferometer on which the filter is based can preferably be tuned, for example, through the ability to adjust the temperature or through mechanical adaptation. In this way, desired spectra can be selected flexibly.

Suitable thin-film filters can also preferably be used. These are particularly easy to manufacture and very compact. In particular, when the IR emitter is manufactured in an integrated manner in a production process, the production of such a thin-film filter can be easily integrated into the process. This reduces costs.

Also a flexible combination of thin-film filters or a thin-film filter tunable, for example, using the temperature method is advantageous.

Filters can also be used for other properties of the IR radiation, e.g. of the polarization.

In a preferred embodiment, the heating element comprises a substrate onto which at least one heatable layer made of a conductive material is applied, on which there are contacts for a current and/or voltage source. The heatable layer is preferably a separate layer to which the base element is applied. The heatable layer can, however, also be formed by the base element.

The substrate preferably forms the base of the heating element. In this case, the substrate can also at least partially comprise further elements of the IR emitter, such as, for example, actuator, base element, dielectric interlayer, cover element, and/or housing elements. The substrate can advantageously be suitably formed by established process steps, in particular from semiconductor and/or microsystem production. Then a heatable layer made of a conductive material can preferably be applied to the substrate or integrated into the substrate, e.g. through doping and/or coating. It is preferred that the heatable layer is brought into contact with a source of electrical energy in order to produce an electrical contact.

In a further preferred embodiment of the modulatable infrared emitter, the substrate is selected from a group comprising silicon, monocrystalline silicon, polysilicon, silicon dioxide, silicon carbide, silicon germanium, silicon nitride, nitride, germanium, carbon, gallium arsenide, gallium nitride, and/or indium phosphide. These materials are especially easy and inexpensive to process in semiconductor and/or microsystem production and are also well-suited for mass production. These materials are also particularly suitable for doping and/or coating in order to achieve the desired electrical, thermal, and/or radiation properties in certain areas.

In a further preferred embodiment of the modulatable infrared emitter, the conductive material for forming the heatable layer is selected from the group comprising platinum, tungsten, (doped) tin oxide, monocrystalline silicon, polysilicon, molybdenum, titanium, tantalum, titanium-tungsten alloy, metal silicide, aluminum, graphite, and/or copper. These materials have the desired thermal, electrical, mechanical, and/or radiation properties and are also particularly easy and inexpensive to process.

In a further aspect, the invention relates to a production method for an infrared emitter as described above, the production comprising the following steps:
  Etching a substrate;
  Depositing a conductive material onto the substrate to form a heatable layer and contacting the heatable layer;
  Depositing a conductive material to form the base element;
  Depositing a dielectric material to form a dielectric interlayer
  Depositing a conductive material to form a cover element and/or structuring the cover element as a metamaterial with periodically arranged unit cells, in which preferably
  an etching and/or a structuring is selected from the group comprising dry etching, wet chemical etching, and/or plasma etching, in particular reactive-ion etching, deep reactive-ion etching (Bosch process); and/or
  the depositing is selected from the group comprising physical vapor deposition (PVD), in particular thermal evaporation, laser beam evaporation, arc evaporation, molecular beam epitaxy, sputtering, chemical vapor deposition (CVD), and/or atomic layer deposition (ALD).

For example, one of the preferred materials mentioned above can be used. During etching, a blank, for example a wafer, can be shaped into the desired basic shape of a heating element. In the next steps, the conductive material for the heatable layer, the conductive material for forming a base element, and a conductive material for forming a cover element can be deposited.

Should a further structuring of the conductive material be desired, in particular for the cover element, this can be done, for example, through further etching processes. Additional material can also be deposited or doping can be carried out using conventional methods.

For contacting the heatable layer, a suitable material, such as, e.g., copper, gold, and/or platinum can be deposited on the conductive material through common processes. Physical vapor deposition (PVD), chemical vapor deposition (CVD), or electrochemical deposition can preferably be used for this purpose.

In this way, especially fine structures can be produced which have dimensions in the nanometer or micrometer range. These production steps have also proven to be particularly effective and are part of standard process steps in semiconductor processing.

In a further preferred embodiment of the manufacturing method, etching and/or structuring is selected from the group comprising dry etching, wet chemical etching, and/or plasma etching, in particular reactive-ion etching, deep reactive-ion etching (Bosch process); and/or the depositing selected from the group comprising physical vapor deposition (PVD), in particular thermal evaporation, laser beam evaporation, arc evaporation, molecular beam epitaxy, sputtering, chemical vapor deposition (CVD), and/or atomic layer deposition (ALD).

These processes are particularly suitable for the production of fine structures with dimensions in the micrometer range. In particular, the Bosch process can produce very fine structures with a high aspect ratio, which are advantageous for a compact, efficient, and integrated structure of the components of the IR emitter.

In a further aspect, the invention relates to a system, comprising
a) a modulatable infrared emitter according to the invention or preferred embodiments thereof
b) a control device
in which the control device is configured for regulating the actuator for a relative movement of the cover element and the base element between a first and second position in order to modulate the intensity of the emission of the infrared emitter.

The control device preferably enables an input and converts this input into suitable control signals. An input can be, for example, a desired spectrum, a desired resonance wavelength, a desired intensity, the modulation depth, and/or the modulation frequency. The control device primarily generates corresponding analog electrical signals which are passed on to the actuator and/or the micro-heating element in order to generate the desired IR radiation.

However, more complex signals can also be used as the input, which specify an exact amplitude curve of the outgoing IR radiation over time for a desired spectrum. The control device then also preferably provides the control signals suitable for generating the desired, modulated IR radiation.

The control device is configured, in particular, to regulate the actuator for the relative movement between the base element and the cover element between (at least) one first and (at least) one second position. For this purpose, electrical signals are generated that trigger the required translational movement of the at least one actuator.

The control device preferably comprises a control loop, in which a discrepancy between the desired control and the actual movement of the actuator and/or heating of the heating element can be corrected by means of a feedback mechanism.

It can be preferred that the temperature profile of the heating element can also be regulated by the control device for the additional, slow modulation of the IR radiation.

The control device of the system can be present either externally or integrated on the IR emitter.

The control device preferably comprises a processor, for example a microprocessor. Other integrated circuits that are used for control in digital electronics can also be used.

The use of such a system comprising a suitable control device can considerably simplify the desired use of the IR emitter. For example, suitable spectroscopy signals can be designed on a PC. The desired signals are transmitted to the control device via the input. The control signals are generated by this, which ensures a corresponding IR signal in high compliance with the theoretical specifications.

A control device, in particular in the form of a controller integrated in the emitter, is very compact and easy to use. For the input, the control device preferably has a suitable interface for connection, for example, to a computer. It can also be desired that data can also be transmitted from the controller to the input device via this interface, such as the current temperature of the heating element, the modulation frequency, or other status information.

In a further preferred embodiment of the system, the control device is configured to regulate the temperature of the heatable areas of the micro-heating element, preferably in a range between 50° C. and 1000° C.

Such a control device is preferably able to provide the heating element with suitable electrical power. In particular, it should be possible to set the temperature with sufficient accuracy and/or keep it constant. A control mechanism with a feedback loop can be used for this. To measure the current temperature of the heating element, at least one temperature sensor, for example, can be integrated at a suitable point on the element.

In a further preferred embodiment of the system, the control device is configured to regulate the actuator for an oscillating relative movement of the cover element and the base element between a first and a second position, in which preferably a modulation frequency of the emitted infrared radiation between 10 Hz and 100 kHz is achieved.

It is preferred that the translational movement triggered by the actuator is repeated regularly between a first and a second position, so that there is an oscillation between the positions and the translational movement has a periodicity. At the end of the translational movement, the starting point of the movement should preferably be reached again and the movement should be carried out again in the following period. The frequency of the oscillating movement preferably determines the resulting modulation frequency of the power intensity of the emitted infrared radiation.

The translation frequency and thus the modulation frequency can also be set continuously within the scope of the electronic resolution and/or bandwidth of the control device and/or the actuator. The modulation frequency can thus preferably be varied over time.

It can furthermore be preferred that not only the translation frequency but also the translation amplitude is varied within the scope of the movement possibilities of the actuator.

For example, the vertical changes in distance between the cover element and the dielectric interlayer or the degree of overlap between the cover element and the base element can be varied. This enables the emissivity and consequently the modulation depth to be set in a time-variable manner in the positions approached.

This results in a system which enables the modulation frequency and modulation depth of the IR radiation to be varied very flexibly and efficiently.

In a further preferred embodiment of the system, the control device is configured to regulate the actuator for an oscillating relative movement of the base element and the cover element such that a modulation frequency of the emitted infrared radiation between 10 Hz and 100 kHz is achieved, with between 100 Hz and 20 kHz being especially preferred.

For this purpose, it is particularly preferred that all required components, such as the control device, actuator, etc., enable the required bandwidth.

The frequencies mentioned have proven to be particularly effective for the preferred applications in the field of spectroscopy. In particular, these frequencies have proven to be particularly suitable for use in photoacoustic spectroscopy, since they cover a large range of acoustic frequencies, the generation of which is the focus of this spectroscopy method.

In a further aspect, the invention relates to a method for the modulated emission of infrared radiation, comprising
    providing a modulatable infrared emitter according to the preceding description;
    heating the heating element to emit infrared radiation;
    controlling the actuator for a relative movement of the cover element and the base element between a first and second position in order to modulate the intensity of the emission of the infrared emitter.

The average person skilled in the art recognizes that technical features, definitions, and advantages of preferred embodiments of the IR emitter according to the invention and of the system also apply to the method according to the invention.

In a further aspect, the invention relates to the use of a modulatable infrared emitter according to the preceding description or the use of a system according to the preceding description for a spectroscopic method, selected from the group comprising photoacoustic spectroscopy and/or infrared spectroscopy.

A compact, long-lasting IR emitter that can be modulated at high speed is of interest for a large number of applications. For photoacoustic spectroscopy in particular, many applications are conceivable that do not take place in the laboratory and have to function under everyday conditions. Examples include the field of environmental sensors for the detection of (harmful) substances in the ambient air or as a warning device for toxic gases such as carbon monoxide.

Due to the high modulation frequencies of a few kHz, significantly improved signal-to-noise ratios can be achieved compared to direct electrical modulation of the heating element, which enables reliable measurements.

In a further aspect, the invention relates to a photoacoustic spectroscope for analyzing gas, comprising
  a modulatable infrared emitter according to the preceding description,
  an analysis volume that can be filled with gas,
  a sound detector,
wherein the analysis volume is arranged between the infrared emitter and the sound detector, so that the infrared radiation emitted in a modulatable manner by the infrared emitter can be used for photoacoustic spectroscopy of the gas.

One skilled in the art knows how photoacoustic spectroscopy is carried out and which components are used in it. The modulatable infrared emitter is preferably arranged and configured in such a way that infrared radiation emitted by the infrared emitter strikes the gas in the analysis volume. If the modulated irradiation takes place with an infrared wavelength which corresponds to the absorption spectrum of a molecule in the gas, a modulated absorption takes place, which leads to heating and cooling processes, the time scales of which reflect the modulation frequency of the radiation. According to the photoacoustic effect, the heating and cooling processes cause the gas to expand and contract, causing sound waves at the modulation frequency. These can then be measured by the sound detector. The power of the sound waves is preferably directly proportional to the concentration of the absorbing gas. The sound detector or sound pressure detector can preferably be a microphone. Likewise, other structures that can be set in vibration by the sound waves can be used as sound detectors, such as, e.g., membranes or vibration bars.

In this case, the gas to be analyzed is located in an analysis volume that can be filled with gas. In a preferred embodiment, this is a volume (or chamber) which is at least partially closed or closable to the outside in which the gas is located or can be introduced, e.g., through a closable opening in the form of a closure and/or valve and/or through a supply line. However, it can also be a completely closed or closable volume or chamber which has at least one closable opening, preferably two, for introducing and/or discharging the gas to be analyzed. In this way, the gas to be analyzed can be localized very well, in particular in a beam range of infrared radiation.

The analysis volume can preferably also be at least partially open. As a result, particularly a gas atmosphere surrounding the spectroscope, to which the analysis volume is at least partially open, can be measured and its composition can be checked. This is particularly interesting for applications in the field of pollutant measurement, but also, for example, for military applications or for counter-terrorism, e.g., from a poison gas attack.

In this case, it is advantageous that the analysis volume is well-defined so that the infrared emitter, the analysis volume, and the sound detector are arranged in such a way that the emittable infrared radiation that can be modulated by the infrared emitter can excite the gas in the analysis volume to form sound pressure waves, which can be measured using the sound pressure detector.

The analysis volume is preferably in the beam path of the infrared emitter. This preferably means that the intensity of the beam essentially or at least partially strikes the side of the analysis volume facing the emitter. Partially means preferably at least 40%, preferably at least 50%, 60%, 70%, 80%, or more.

In a preferred embodiment, the infrared emitter can be oriented from the outside to a preferred area of the analysis volume. If it is necessary to radiate through an outer wall of the volume in order to excite a gas inside, the outer wall is preferably at least substantially transparent in this area for the IR radiation. The infrared emitter can, however, also be arranged inside the analysis volume.

The analysis volume can preferably be filled with gas. This means that, even in the case of an at least partially closed or closable volume, there is a preferably closable opening for filling. Preferably, a gas flow can also be realized in that the analysis volume, for example, has an inlet and an outlet. Thus, either a continuous gas flow can be realized in the volume or a discontinuous gas flow, in which, for example during a filling or gas exchange phase, a filling or an exchange of the gas can be carried out in the analysis volume. In an analysis phase, the gas flow is preferably interrupted so that the photoacoustic spectroscopy can take place. If different gases are to be analyzed at different times, this can preferably be achieved by such a structure. A cleaning gas for cleaning the volume of any gas residue can preferably be supplied between two gases to be analyzed.

In the case of an analysis volume which is at least partially open and thus preferably allows permanent gas exchange with an environment, the analysis volume is filled by interaction with a gas atmosphere in the environment.

An analysis volume can preferably comprise a sample chamber and a reference chamber, which are connected or can be connected by a connecting channel.

In the case of an embodiment of an analysis volume which has a sample chamber and a reference chamber, it can be preferred to have at least one sound detector in each chamber in order to measure separately in each chamber and thus to be able to exclude sources of interference, for example external sound pressure waves, which do not come from the IR radiation absorbed in the sample chamber, preferably after the measurement.

Likewise, it can be preferred that the infrared emitter irradiates the sample chamber and not the reference chamber, and a connecting channel in which a sound detector is located is present between the sample chamber and reference chamber. This embodiment is distinguished by particularly precise photoacoustic spectroscopy, since, for example, sound from undesired sound sources is excluded or not included in the measurement and/or the evaluation of the measurement. The sample volume and a reference volume can preferably have essentially the same dimensions in order to implement an accurate differential measurement method.

The same gas can be found in the sample volume and reference volume. It can also be preferred that different gas is included in the sample volume and in the reference volume, a gas with known properties being present in the reference volume and a gas to be analyzed being present in the sample volume. By using two volumes and at least one sound pressure detector, an improved elimination of sources of error, for example undesired sound waves, can occur because they act on both volumes, and the sound pressure detector arranged between the volumes preferably essentially only detects the sound pressure waves caused by the IR radiation relevant for photoacoustic spectroscopy in the sample volume as a difference signal between the sample volume and the reference volume.

Due to the IR emitter being compact and modulatable at high-frequency, which is not known from the prior art, the entire structure can always be made particularly compact and suitable for everyday use for different variants of a photoacoustic spectroscope. Due to the high modulation frequencies, the analysis options are also extremely diverse, and in particular the signal-to-noise ratio can be increased. A typical 1/f noise can thus be significantly reduced, for example, in sound detectors, such as microphones.

In a preferred embodiment, the photoacoustic spectroscope comprises at least two or more modulatable infrared emitters according to the description above, the resonance wavelengths of the two or more modulatable infrared emitters differing. As stated above, the resonance wavelength at which a high emission of infrared radiation occurs in the second position can be set in particular by suitable structuring of the metamaterial or the periodically repeating unit cells.

By using two or more modulatable infrared emitters with different resonance wavelengths, different molecules in the gas can be analyzed at the same time. Since the or two or more modulatable infrared emitters also have separate actuators, they can also preferably be operated by means of different modulation frequencies, whereby the sound waves of the different molecules can be detected separately in a particularly precise manner. Due to the compact design, a miniaturized photoacoustic spectroscope can be provided, which is characterized by a wide range of simultaneously detectable molecules with the highest accuracy.

DETAILED DESCRIPTION

The invention is to be explained in more detail below using examples and figures, without being restricted to these.

DETAILED DESCRIPTION OF THE FIGURES

Figure 1:
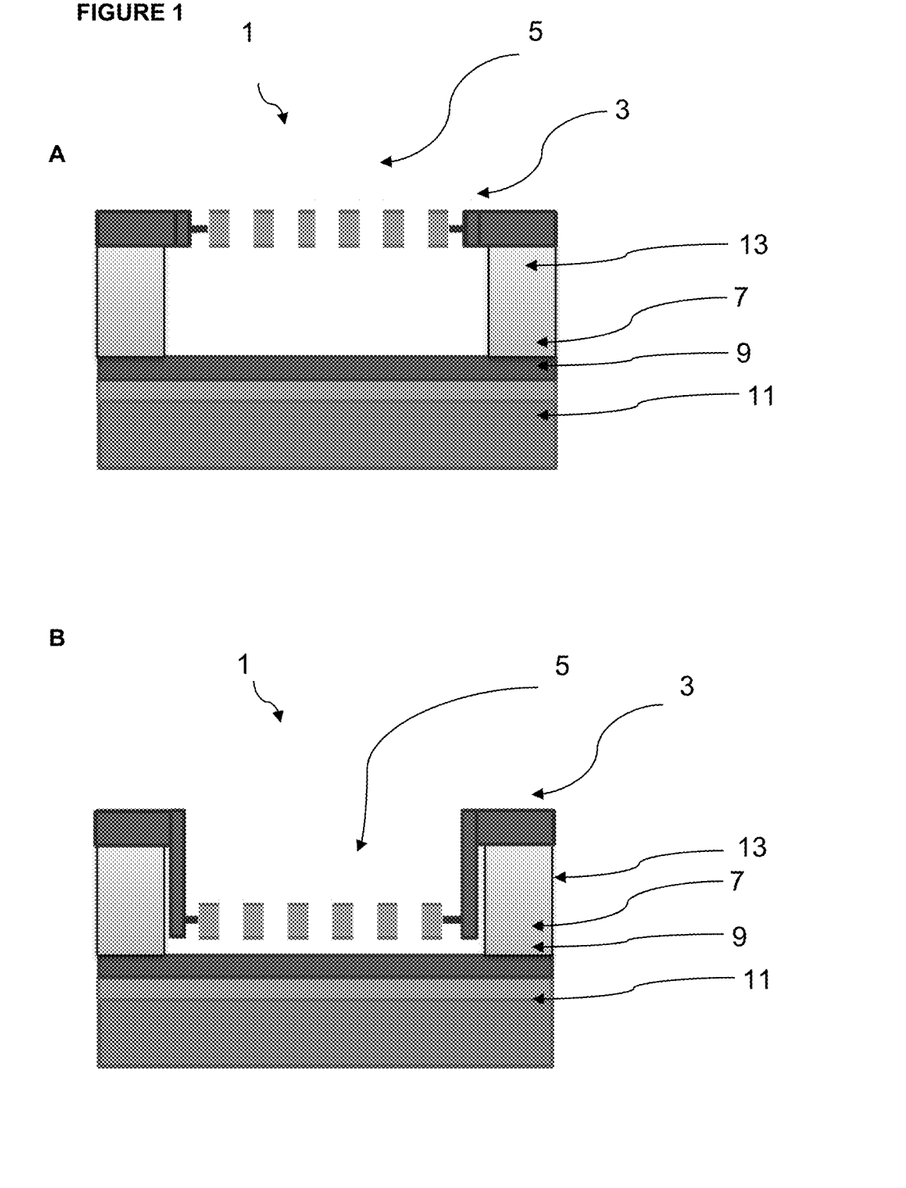
FIG. 1 shows a schematic representation of a cross-section of a preferred embodiment of the modulatable infrared emitter. (A) cover element 5 is kept at a greater distance above the dielectric interlayer 7. (B) cover element 5 is kept at a lesser distance above the dielectric interlayer 7.

FIG. 1 shows a schematic representation of a preferred embodiment of a modulatable infrared emitter 1 in cross-section. A layer structure comprising a planar base element 9, a dielectric interlayer 7, and a planar cover element 5 made of a structured metamaterial is present on a heating element 11. The heating element 11 may comprise, for example, an Si substrate onto which a heatable layer made of a conductive material is applied, on which there are contacts for a current and/or voltage source. However, it can also be preferred that the base element 9 functions as a heatable layer and is contacted for this purpose. The base element 9 and the cover element 5 are preferably made from a conductive material, particularly preferably from a metal.

The cover element 5 is coupled to actuators 3, which are configured for a vertical translational movement of the cover element 5 with respect to the base element and can control at least two positions.

In a first position (FIG. 1A), the cover element 5 is kept at a greater distance above the dielectric interlayer 7 than in a second position (FIG. 1B).

For this purpose, in the embodiment shown, there is a spacing frame 13 on the dielectric interlayer 7, which defines the vertical distance between the cover element 5 and the dielectric interlayer 7 in the first position. The spacing frame 13 can be, for example, a nitride or oxide layer, which is applied along the border of the dielectric interlayer 7 at a defined height. The actuators 3 are coupled both to the spacing frame 13 and to the cover element 5 and are configured to hold the cover element 5 at the level of the upper end of the spacing frame 13 in a first position, while the cover element 5 is lowered toward the dielectric interlayer 7, preferably to the point of contacting, in the second position.

The actuators 3 are preferably MEMS actuators, especially preferably electrostatic MEMS actuators, in which the cover element 5 can be moved into a first or second position in a targeted manner, for example by applying a voltage.

The translational movement of the cover element 5 controlled by the actuators 3 modulates the intensity of the infrared emitter 1.

During the operation of the infrared emitter 1, the heating element 11 is preferably controlled to a temperature in a range of from 50° to 1000°. The resulting emitted infrared radiation depends on the distance at which the cover element 5 made of a structured metamaterial is located above the dielectric interlayer 7 or the base element 9.

In the second position shown in FIG. 1B, the cover element 5 is located at a distance of preferably less than 200 nm, especially preferably at a distance which corresponds to a contact between the two elements. In this state, the cover element 5 made of a structured metamaterial, the dielectric interlayer 7, and the base element 9 on the heating element 11 preferably form a metamaterial perfect absorber, whereby a particularly high emissivity is achieved for one or more preferred resonance wavelengths. In other words, an electromagnetic resonance occurs in the second position, which enables the infrared radiation to be coupled to a specific resonance wavelength.

The vertical distance in the first position (FIG. 1A) is selected such that no resonant coupling can occur and the infrared emitter 1 has a low emissivity.

The change provided by the actuators 3 between a first (non-resonant) and a second (resonant) position thus modulates the intensity of the emitted infrared radiation. In simple terms, the IR emitter 1 is "OFF" in the first position and "ON" in the second position. A high-frequency modulation between the two states in the kHz range can advantageously be achieved using MEMS actuators, as a result of which the infrared emitter described is particularly suitable for applications in infrared spectroscopy.

Figure 2:
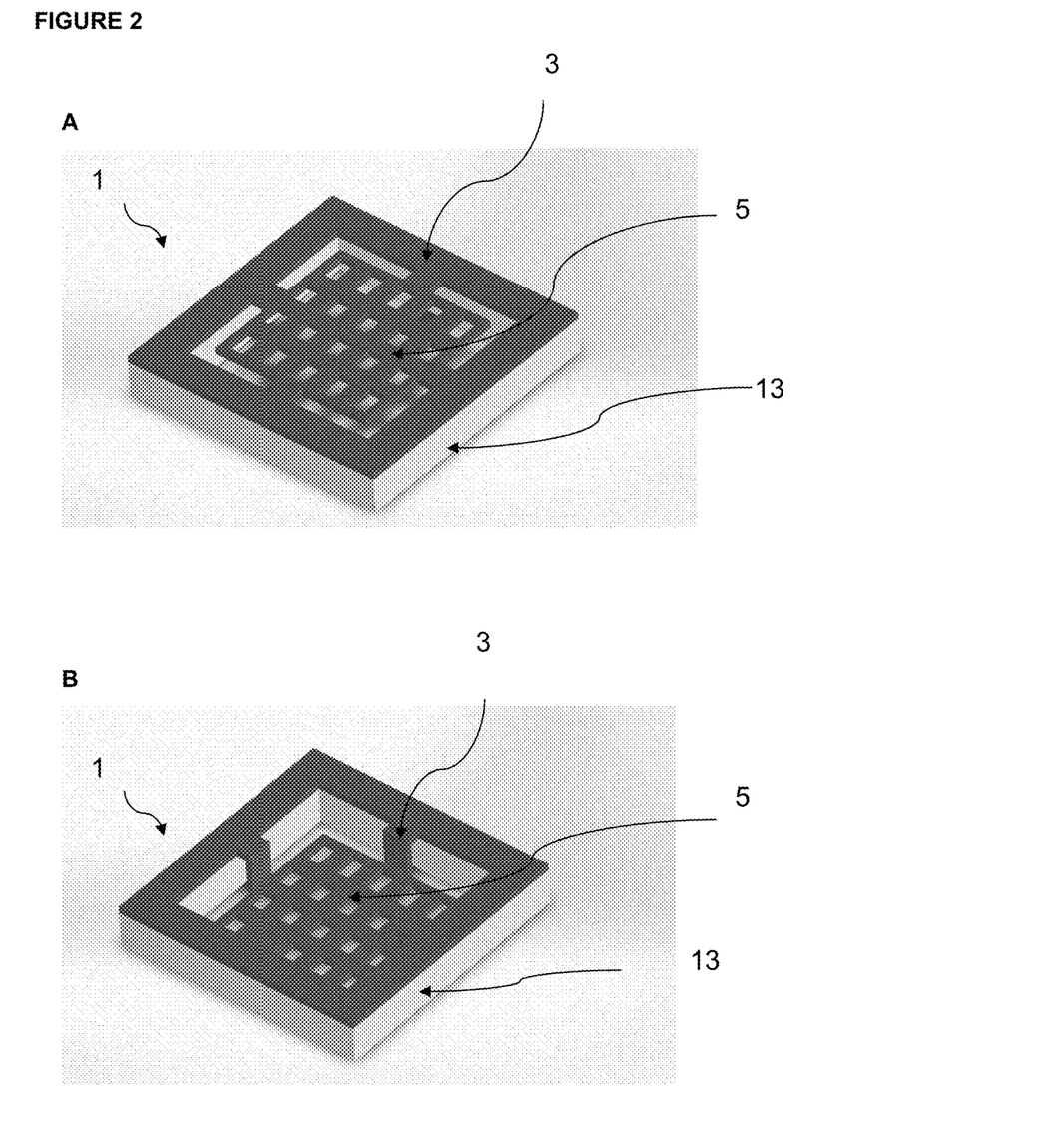
FIG. 2 shows a schematic 3D view of a preferred embodiment of the modulatable infrared emitter. (A) Four MEMS actuators 3 are preferably each coupled to the spacing frame 13 and to the cover element 5 and configured for a vertical relative movement of the cover element 5 from a first position. (B) Four MEMS actuators 3 are preferably each coupled to the spacing frame 13 and to the cover element 5 and configured for a vertical relative movement of the cover element 5 from a second position.
Figure 3:
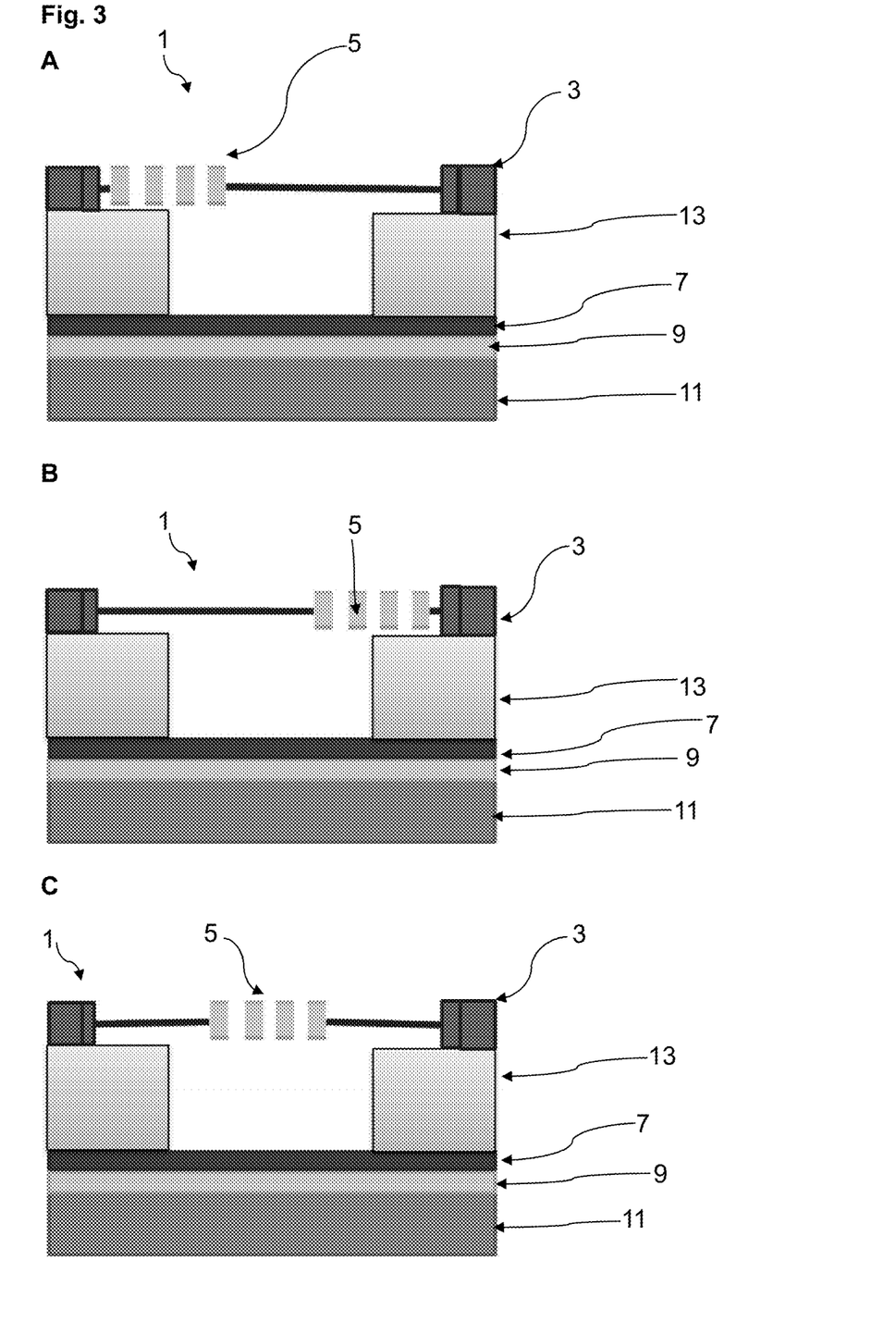
FIG. 3 shows a horizontal actuating mechanism. (A and B) Cover element 5 made of a structured metamaterial and base element 9 have in a first position a reduced degree of overlap (e.g., less than 40%). (C) The overlap in between cover element 5 and base element 9 is 100%, such that a resonant emission takes place.

FIG. 2 shows a schematic 3D view from above of a preferred embodiment of a modulatable infrared emitter 1. This is preferably an embodiment of a modulatable infrared emitter 1 as was explained with reference to the cross-section shown in FIG. 1. As can be seen in the 3D view, the preferred infrared emitter 1 comprises four MEMS actuators 3, which are installed on the outer sides of the cover element 5. The four MEMS actuators 3 are preferably each coupled to the spacing frame 13 and to the cover element 5 and configured for a vertical relative movement of the cover element 5 from a first position (FIG. 2A) to a second position (FIG. 2B). The use of the four MEMS actuators 3 enables the cover element 5 to be lowered particularly quickly and reliably to a desired distance.

As explained with regard to FIG. 1, the vertical lowering of the cover element 5 made of structured metamaterial onto the dielectric interlayer (not shown) results in a resonant emission of the infrared radiation at one or more preferred resonance wavelengths. In the schematic illustration, the structuring of the metamaterial is indicated by rectangular unit cells. They are primarily used for illustration purposes and, as described above, different shapes and/or dimensions of the unit cells can be used in order to ensure effective resonant emission in the second position.

LIST OF REFERENCE NUMERALS

1 Modulatable infrared emitter
3 Actuator
5 Cover element made of structured metamaterial
7 Dielectric interlayer
9 Base element made of a conductive material
11 Heating element
13 Spacing frame

REFERENCES

[1] Liu et al.: *Micromachined tunable metamaterials: a review*, Journal of Optics 14, 114009, 2012.
[2] Zheludev et al.: From metamaterials to metadevices, Nature Materials, Vol 11, 2012.
[3] Tao et al.: *MEMS Based Structurally Tunable Metamaterials at Terahertz Frequencies*, J Infrared Milli Terahz Waves Vol 32, 580-595, 2011.
[4] Turpin et al.: *Reconfigurable and Tunable Metamaterials: A Review of the Theory and Applications*, International Journal of Antennas and Propagation, Volume 2014, Article ID 429837, 2014.
[5] Hildenbrand et al.: *Micromachined Mid-Infrared Emitter for Fast Transient Temperature Operation for Optical Gas Sensing Systems*. IEEE Sensors Journal, 10 (2), 2010.
[6] Spannhake et al.: *High-temperature MEMS Heater Platforms: Long-term Performance of Metal and Semiconductor Heater Materials*, Sensors 2006, 6, 405-419.
[7] Harald A. Beck, *Anwendung der Photoakustischen Spektroskopie in der Prozess—und Umweltanalytik, Dissertation* [*Application of Photoacoustic Spectroscopy in Process and Environmental Analysis, Dissertation*], Technical University of Munich, 2003.
[8] Pusch et al.: *A highly efficient CMOS nanoplasmonic crystal enhanced slow-wave thermal emitter improves infrared gas-sensing devices*, Nature Scientific Reports, 5:17451, 2015.
[9] Lochbaum et al.: *On-Chip Narrowband Thermal Emitter for Mid-IR Optical Gas Sensing, ACS Photonics*, 4, 1371-1380, 2017.
[10] Tsai, et al.: *Reflection and emission properties of an infrared emitter*, Optics Express, Vol. 15, No. 22, 2007.
[11] V. G. Veselago, Sov. Phys. Usp. 1968, 10, 509.
[12] J. B. Pendry, A. J. Holden, D. J. Robbins, W. J. Stewart, IEEE Trans. Microwave Theory Tech. 1999, 47, 2075.
[13] N. I. Landy, S. Sajuyigbe, J. J. Mock, D. R. Smith, W. J. Padilla, Phys. Rev. Lett. 2008, 100, 207402.
[14] X. Liu, T. Starr, A. F. Starr, W. J. Padilla, Phys. Rev. Lett. 2010, 104, 207403.
[15] Claire M. Watts, Xianliang Liu, and Willie J. Padilla. Metamaterial Electromagnetic Wave Absorbers, Adv. Mater. 2012, 24, OP98-OP120.
[16] I. Puscasu, W. L. Schaich, Appl. Phys. Lett. 2008, 92, 233102.
[17] Qu et al. Micromachines 2016, 7, 14; doi:10.3390/mi7010014.
[18] T. Inoue, M. de Zoysa, T. Asano, and S. Noda, *Realization of narrowband thermal emission with optical nanostructures*, Optica vol. 2, no. 2015.
[19] X: Liu and W. J. Padilla, *Reconfigurable room temperature metamaterial infrared emitter*, Optica, vol. 4, no. 4, 2017.

The invention claimed is:
1. A modulatable infrared emitter, comprising
a heating element;
a planar base element made of a conductive material;
a dielectric interlayer;
a planar cover element made of a conductive material; and
an actuator,
wherein the cover element is a structured metamaterial with periodically arranged unit cells and the actuator is configured for relative movement of the cover element and the base element between a first and second position in order to modulate the intensity of the emission of the infrared emitter,
wherein the relative movement comprises a horizontal translational movement of the cover element and/or base element orthogonal to the emission direction of the infrared emitter, which changes the degree of overlap between the cover element and the base element.

2. The modulatable infrared emitter according to claim 1, wherein the unit cell comprises a resonator which is formed by bracing the conductive material, wherein the resonator has the shape of a split ring resonator (SRR), an electric ring resonator (ERR), a cross, a square, a circle, a hexagon, and/or a combination of these shapes.

3. The modulatable infrared emitter according to claim 1, wherein the cover element is made from a metal and/or wherein the dielectric interlayer is made of a material selected from the group consisting of aluminum nitride, silicon nitride, aluminum oxide, silicon oxide, titanium dioxide, and tantalum oxide.

4. The modulatable infrared emitter according to claim 1, wherein the cover element and base element have a degree of overlap of less than 40% in the first position, and the cover element and base element have a degree of overlap of more than 40% in the second position.

5. A production method for an infrared emitter according to claim 1, wherein the production comprises the following steps:
   etching a substrate;
   depositing a conductive material onto the substrate to form a heatable layer and contacting the heatable layer;
   depositing a conductive material to form the base element;
   depositing a dielectric material to form a dielectric interlayer;
   depositing a conductive material to form a cover element and/or structuring the cover element as a metamaterial with periodically arranged unit cells.

6. A method for the modulated emission of infrared radiation, comprising
   providing a modulatable infrared emitter according to claim 1;
   heating the heating element to emit infrared radiation;
   controlling the actuator for a relative movement of the cover element and the base element between a first and second position in order to modulate the intensity of the emission of the infrared emitter.

7. A method of performing photoacoustic spectroscopy and/or infrared spectroscopy comprising using a modulatable infrared emitter according to claim 1.

8. A photoacoustic spectroscope for analyzing gas, comprising
   a modulatable infrared emitter according to claim 1;
   an analysis volume that can be filled with gas; and
   a sound detector,
   wherein the analysis volume is arranged between the infrared emitter and the sound detector, so that the infrared radiation emitted in a modulatable manner by the infrared emitter can be used for photoacoustic spectroscopy of the gas.

9. A system, comprising:
   a modulatable infrared emitter comprising:
   a heating element;
   a planar base element made of a conductive material;
   a dielectric interlayer;
   a planar cover element made of a conductive material; and
   an actuator,
   wherein the cover element is a structured metamaterial with periodically arranged unit cells and the actuator is configured for relative movement of the cover element and the base element between a first and second position in order to modulate the intensity of the emission of the infrared emitter;
   a control device,
   wherein
   the control device is configured for regulating the actuator for a relative movement of the cover element and the base element between a first and second position in order to modulate the intensity of the emission of the infrared emitter,
   wherein the control device is configured to regulate the actuator for an oscillating relative movement of the cover element and the base element between a first and a second position.

10. A method of performing photoacoustic spectroscopy and/or infrared spectroscopy comprising using a system according to claim 9.

11. A photoacoustic spectroscope for analyzing gas, comprising
   a system according to claim 9;
   an analysis volume that can be filled with gas; and
   a sound detector,
   wherein the analysis volume is arranged between the infrared emitter and the sound detector, so that the infrared radiation emitted in a modulatable manner by the infrared emitter can be used for photoacoustic spectroscopy of the gas.

12. The system according to claim 9, wherein the actuator is a MEMS actuator.

13. The system according to claim 9, wherein the infrared emitter comprises at least four MEMS actuators, which are installed on the outer sides of the cover element and are configured to control the relative movement of the cover element and the base element between the first and second position simultaneously.

14. The system according to claim 9, wherein the cover element is at a distance of at least 500 nm from the dielectric layer in the first position and it is at a distance of at most 200 nm from the dielectric layer in the second position.

15. The system according to claim 9, wherein the emissivity in the direction of the surface normal of the cover element for at least one resonance wavelength, in a range of from 1 μm to 10 μm, is higher in the second position than in the first position by a factor of 2.

16. The system according to claim 15, wherein the emissivity in the direction of the surface normal of the cover element for at least one resonance wavelength, in a range of from 1 μm to 10 μm, has a value of more than 0.7, in the second position and a value of less than 0.4 in the first position.

17. The system according to claim 9, wherein the unit cell comprises a resonator which is formed by bracing the conductive material, wherein the resonator has the shape of a split ring resonator (SRR), an electric ring resonator (ERR), a cross, a square, a circle, a hexagon, and/or a combination of these shapes.

18. The system according to claim 9, wherein the unit cells form a two-dimensional periodic lattice, wherein the lattice angle is between 60° and 120° and the two lattice constants are between 5% and 40% of a resonance wavelength.

19. The system according to claim 9, wherein the cover element is made from a metal and/or wherein the dielectric interlayer is made of a material selected from a group comprising aluminum nitride, silicon nitride, aluminum oxide, silicon oxide, titanium dioxide, and tantalum oxide.

20. The system according to claim 9, wherein the cover element, the dielectric interlayer, and/or the base element have a layer thickness between 100 nm and 1500 nm.

* * * * *